United States Patent [19]

Van Albert et al.

[11] Patent Number: 5,243,540
[45] Date of Patent: Sep. 7, 1993

[54] COMPUTER-DRIVEN AMINO ACID INDEXER FOR PEPTIDE SYNTHESIS

[75] Inventors: Stephen A. Van Albert; Jaime M. Lee; Jeffrey A. Lyon, all of Silver Spring; John M. Carter, Gaitherburg, all of Md.

[73] Assignee: The United States of America as represented by the Secretary of the Army, Washington, D.C.

[21] Appl. No.: 679,990

[22] Filed: Apr. 3, 1991

[51] Int. Cl.⁵ .................... G06F 15/46; C12N 15/00
[52] U.S. Cl. ................................. 364/500; 422/116
[58] Field of Search ............... 364/413.01, 496, 500, 364/502; 422/116

[56] References Cited

U.S. PATENT DOCUMENTS

| | | | |
|---|---|---|---|
| 4,668,476 | 5/1987 | Bridgham et al. | 364/500 |
| 4,708,871 | 11/1987 | Geyson | 930/222 |
| 4,744,037 | 5/1988 | Niina et al. | 364/500 |
| 4,816,513 | 3/1989 | Bridgham et al. | 422/134 |
| 5,081,584 | 1/1992 | Omichinski et al. | 364/497 |

*Primary Examiner*—Thomas G. Black
*Assistant Examiner*—Michael Zanelli
*Attorney, Agent, or Firm*—Anthony T. Lane; Werten F. W. Bellamy; John F. Moran

[57] ABSTRACT

An automated, computer-driven amino acid indexer for peptide synthesis uses a programmed computer, a circuit board controller, and a combination of microtiter sample well trays, light emitting diodes to illuminate each sample well, and circuitry to control the illumination of the diodes. The apparatus simplifies technical difficulties present in large-scale laboratory syntheses of peptides by substantially reducing the time required for dispensing amino acids into sample trays and reducing the occurrence of error in the process to negligible levels in typical syntheses. A programmed, automated technique for synthesizing peptides is also provided.

7 Claims, 7 Drawing Sheets

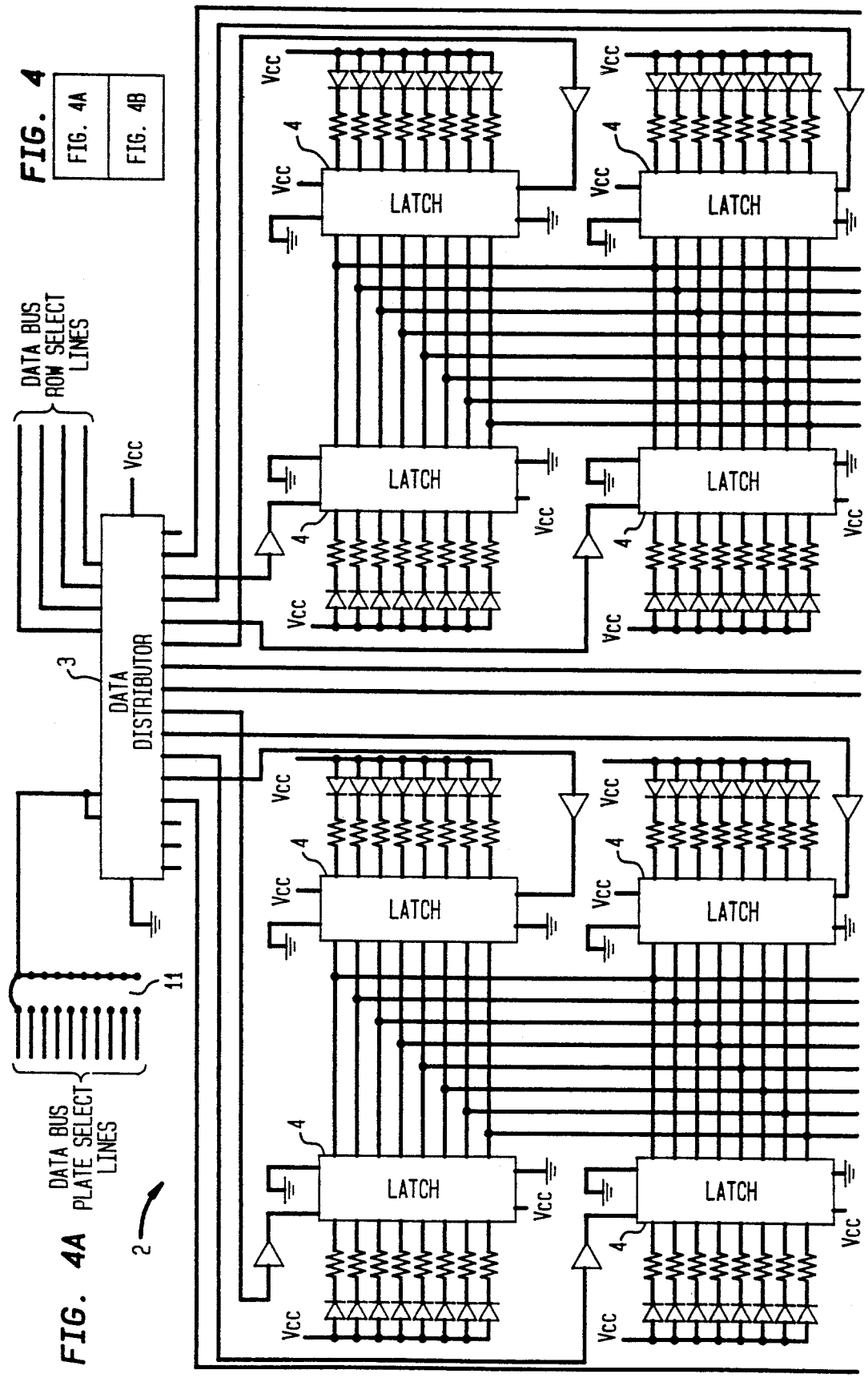

FIG. 6

```
  1 MKKIMLIASA MSALSLPFSA SAIELGEEGL ECGPYAKVGV VGGMITGVES
 51 ARLDPADAEG KKHLSLTNGL PFGGTLAAGM TIAPGFRAEI GVMYLTNITA
101 QVEEGKVKAD SVGETKADSV GGKDAPIRKR FKLTPPQPTI MPISIAVRDF
151 GIDIPNQTSA ASTSRSLRLN DEQRAAARIA WLKNCAGIDY RVKNPNDPNG
201 PMVINPILLN IPQGNPNPVG NPPQRANPPA GFAIHNHEQW RHLVVGLAAL
251 SNANKPSASP VKVLSDKITQ IYSDIKHLAD IAGIDVPDTS LPNSASVEQI
301 QNKMQELNDL LEELRESFDG YLGGNAFANQ IQLNFVMPQQ AQQQGQGQQQ
351 QAQATAQEAV AAAAVRLLNG NDQIAQLYKD LVKLQRHAGI KKAMEKLAAQ
401 QEEDAKNQGE GDCKQQQGTS EKSKKGKDKE AEFDLSMIVG QVKLYADVMI
451 TESVSIYAGV GAGLAYTSGK IDNKDIKGHT GMVASGALGV AINAAEGVYV
501 DIEGSYMYSF SKIEEKYSIN PLMASVSVRY NFGPYAKVGV VGGMITGVES
551 MKKIMLIASA MSALSLPFSA SAIELGEEGL ECGPYAKVGV VGGMITGVES
601 ARLDPADAEG KKHLSLTNGL PFGGTLAAGM TIAPGFRAEI GVMYLTNITA
651 QVEEGKVKAD SVGETKADSV GGKDAPIRKR FKLTPPQPTI MPISIAVRDF
701 GIDIPNQTSA ASTSRSLRLN DEQRAAARIA WLKNCAGIDY RVKNPNDPNG
751 PMVINPILLN IPQGNPNPVG NPPQRANPPA GFAIHNHEQW RHLVVGLAAL
801 SNANKPSASP VKVLSDKITQ IYSDIKHLAD IAGIDVPDTS LPNSASVEQI
851 QNKMQELNDL LEELRESFDG YLGGNAFANQ IQLNFVMPQQ AQQQGQGQQQ
901 QAQATAQAEV AAAAVRLLNG NDQIAQLYKD LVKLQRHAGI KKAMEK
```

KEY TO ONE-LETTER SYMBOLS FOR AMINO ACIDS:

| | | |
|---|---|---|
| A=ALANINE | G=GLYCINE | P=PROLINE |
| R=ARGININE | H=HISTIDINE | S=SERINE |
| N=ASPARAGINE | I=ISOLEUCINE | T=THREONINE |
| D=ASPARTIC ACID | L=LEUCINE | W=TRYPTOPHAN |
| C=CYSTEINE | K=LYSINE | Y=TYROSINE |
| Q=GLUTAMINE | M=METHIONINE | V=VALINE |
| E=GLUTAMIC ACID | F=PHENYLALANINE | |

COMPUTER-DRIVEN AMINO ACID INDEXER FOR PEPTIDE SYNTHESIS

BACKGROUND OF THE INVENTION

1. Field of the Invention

This invention is in the field of solid-phase peptide synthesis. More specifically, this invention relates to a novel computer-driven amino acid indexer for rapidly synthesizing peptide samples on a solid support with very high amino acid sequence accuracy.

2. Description of the Related Art

Solid-phase methods of peptide synthesis have been developed in which proteins of defined amino acid sequence are prepared by the step-wise addition of amino acids in the defined order to a growing peptide chain on a solvent-resistant matrix. De novo design and synthesis of peptides has become an indispensable technique in scientific research for a variety of important reasons.

The design and synthesis of novel and naturally occurring peptides makes it possible to study protein topologies and conformations as well as the kinetics of protein folding. Additionally, many biologically active substances, such as hormones and signal molecules, are peptides. Further peptide synthesis is useful in identifying the receptor sites on cell surfaces where hormones and signal molecules are active. There is keen interest in this field because synthetic peptides may be useful as pharmaceutical agents with a variety of applications, such as vaccines effective against bacterial and viral infections. And synthetic peptides may also be used to identify specific antibody binding sites, known as epitopes, on antigens, disease-inducing foreign organisms or viruses. As a corollary to this last field of endeavor, it is also possible to use synthetic peptides as antigens or as fragments which are effective epitope mimics to stimulate the production of particular antibodies by the host organism (*Scientific American* Feb. 1983:48-56; *Nature* 306:9 [1983]).

The overall immune systems of higher animals comprise very complex interactions of non-specific defensive scavengers (phagocytes), specific defenders (i.e., antibodies), mediators, and modulators. The capability of higher animals to fight a given disease is greatly dependent on the ability of the host's antibodies to recognize antigens and bind them tightly and specifically. This binding activity precipitates a sequence of events that leads to the neutralization and elimination of the organism or virus responsible for the disease. Diseases which are subject to surveillance by the host immune system in this general manner include, by way of example, influenza, tetanus, polio, smallpox, and many cancers. Vaccines and therapeutic compounds are being sought for some cancers, acquired immunodeficiency syndrome (AIDS), hepatitis B, herpes and other diseases. The effects of certain chemical warfare agents are also being studied to determine whether such agents are subject to resistance by antibodies according to the general scheme described herein.

A particularly challenging endeavor in the field of immunology is to characterize mechanism and binding specificity of a host's immune response to a particular peptidic antigen. Each antigen binding site, or epitope, is specific to a particular antibody. Solid-phase peptide synthesis techniques are especially useful in this endeavor, in that a synthetic peptide having the same amino acid sequence as an epitope, or one so similar that it effectively mimics the epitope, will bind an antibody in the same tight and specific manner as will a natural antigen possessing the epitope. Peptide fragments which copy of mimic an epitope can trigger the same immune response as a peptidic antigen containing the epitopic center as well as the genetic material required to replicate itself. Thus, immunization by using peptide fragments substantially reduces the risk of infection or deleterious side effects. By making up sample peptides and mapping their antibody binding characteristics through analytical techniques such as enzyme-linked immunosorbent assay (ELISA) or radioimmuno assay (RIA), it is possible to characterize the antibody reactivity of a large number of peptides and identify those which are active as epitopic centers.

The antibody reactivity mapping technique may be used in conjunction with a technique recently introduced by Hendrik Mario Geysen for synthesizing and testing large numbers of peptides (U.S. Pat. No. 4,833,092, May 23, 1989, *Method for Determining Mimotopes,* and U.S. Pat. No. 4,708,871, Nov. 24, 1987, *Antigenically Active Amino Acid Sequences*). In this technique, peptides are synthesized incrementally backwards according to processes known in the art of peptide synthesis chemistry. An activated derivative of the correct individual amino acid is pipetted onto each growing peptide chain, each peptide being synthesized separately on a plastic pin. An 8×12 or similar matrix of pins may be used in the syntheses. After hundreds of peptides are individually prepared, each on its own respective pin, the pins are assayed by ELISA for antibody reactivity. The peptides made according to this method are typically eight amino acid residues in length and have an overlapping pattern along the entire protein sequence. (The testing of an antigen containing 100 residues in a defined sequence according to the overlapping pattern would require synthesizing eight-residue test samples, beginning with one corresponding to residues 1-8 of the antigen, the next corresponding to residues 2-9 of the antigen, then 3-10, through the last peptide which would correspond to residues 93-100 of the antigen).

Since the pioneering work of R. Bruce Merrifield in developing a solid-phase peptide synthetic method using solvent-resistant polystyrene beads, *Science* 232:341-347 [1986], techniques of peptide synthesis have remained essentially labor-intensive and time-consuming. This means that skilled technicians must spend long periods of time in performing mechanical tasks, such as pipetting amino acid derivatives into a matrix of solvent-resistant wells for incremental growth of peptide chains in desired sequences. Matching the properly ordered amino acid with the proper well in the matrix has remained essentially a manual task. With current techniques, even an experienced technician can suffer from mental fatigue and confusion during synthesis of multiple peptide samples, one hundred to one thousand, for example, while trying to keep the different wells identified and the prescribed amino acid sequences straight. Notwithstanding the experience and skill required of the technicians so employed and the time that such mechanistic processes inherently require, error rates have typically exceeded the rates that are normally considered acceptable in a biochemistry laboratory. It is apparent that committing trained and skilled technicians to laborious and tedious occupations is inefficient and undesirable.

Given the keen interest in peptide synthesis and analysis shown by government, industry, and academic institutions, it is highly apparent that simplified means for peptide synthesis which overcome the technical problems associated with current techniques are needed. Simplification can reduce technical errors in the sequencing of amino acids during synthesis, save time, help to reduce human error evident in tasks such as the set up of synthetic apparatus, and free technical personnel for other tasks. In this invention, an amino acid indexer for peptide synthesis is provided which simplifies the various technical difficulties associated with peptide synthesis and renders the process more efficient by saving time, reducing errors, and lowering the level of skill absolutely required to perform the mechanical functions of peptide synthesis.

SUMMARY OF THE INVENTION

Synthesis of peptides for epitope mapping analysis, vaccine preparation, and other purposes is a vitally important scientific technique which has been characterized by tedious manual labor and relatively high error rates. By automating the indexing of amino acid sequencing and selection, peptide syntheses may be accomplished rapidly with undetectable error.

The present invention is directed primarily to an apparatus for the computer-driven indexing of amino acids for large scale laboratory synthesis of peptides. The apparatus provides computer programmed amino acid selection and sequence indexing with a combination of solvent-resistant sample trays, light means, main circuit control means for receiving indexing signals and translating them into control signals for the light means, and latch circuit board control means for governing the light means in accordance with the signals received from the main circuit control means. In one aspect of the invention, there are ten sample plate arrays each comprising an 8×12 matrix of wells, ten latch circuit control means and ten 8×12 arrays of light means, providing one light means such as a light emitting diode for each sample well. In this aspect, there are sample trays and automated control means for the preparation of 960 different polypeptides.

In another of its aspects, the invention is directed to an automated, computer-driven method for preparing peptides comprised of different amino acid sequences.

BRIEF DESCRIPTION OF THE DRAWINGS

FIG. 6 is the protein sequence upon which the sample peptide syntheses applying the apparatus and method of the invention described in the Example were based.

DETAILED DESCRIPTION OF THE INVENTION

Figure 1:
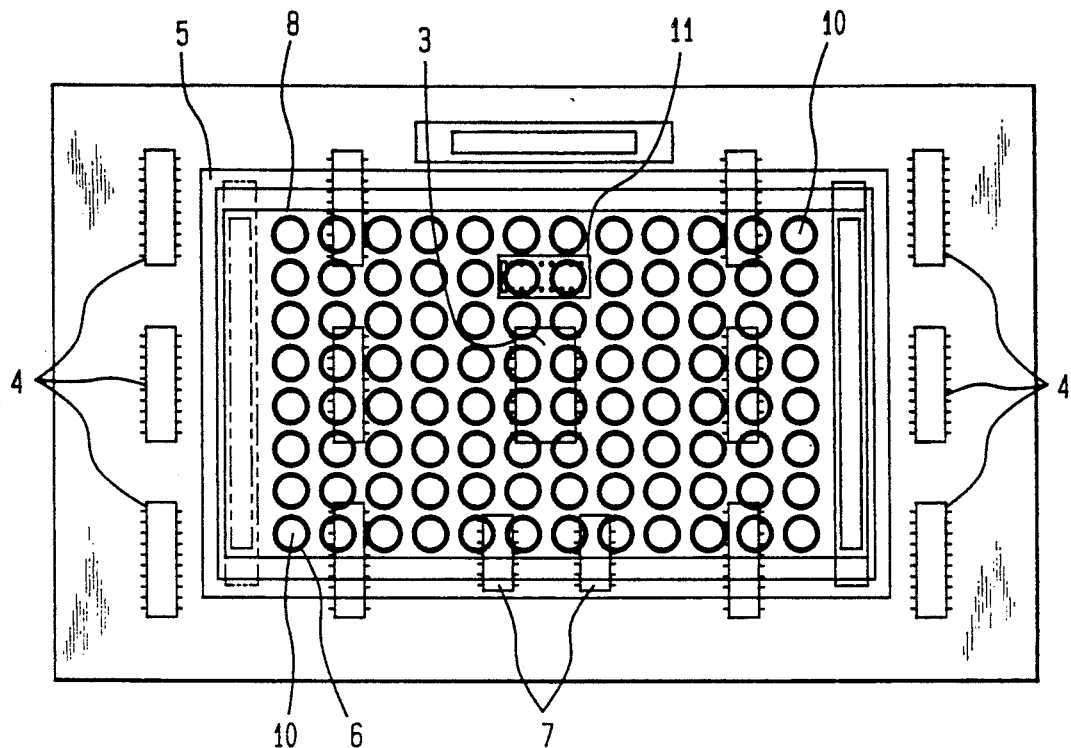
FIG. 1 is a top view of a combination of an LED board support plate, LED indicator board with LED elements, and latch board, of the invention.

This invention pertains to a computer-driven amino acid indexer designed primarily for the synthesis of peptides used in epitope mapping of protein antigens. The indexer of this invention is designed to allow for more rapid synthesis of peptides than by prior art techniques, which are manually intensive procedures, while reducing error to a negligible rate. Standard ELISA and RIA microtiter plates may be used with the indexer of this invention. Computer software can be designed to make the indexer applicable to a wide range of biological and biochemical investigations, including: lymphocyte proliferation, cell surface receptor binding, cytotoxicity, virus plaques, enzyme kinetics, and other procedures often performed in clinical chemistry and microbiology laboratories. Almost any large experiment that requires pseudo-random filling of microtiter plates lends itself to the amino acid indexer of this invention with appropriate software applications. Thus, it is an object of this invention to provide an apparatus for increasing the accuracy and efficiency of peptide synthesis for epitope mapping. It is a further object of the invention to provide an apparatus and a method to aid researchers in the quick, efficient, low cost development of peptides leading to faster vaccine development. Details of various embodiments of the invention will be set forth in detail below.

The amino acid indexer of this invention is designed to simplify various technical problems of matching the twenty different amino acids to potentially hundreds of microtiter plate wells for each day's work of peptide syntheses while incidentally reducing human error in apparatus set-up in some instances. It is well known that error rates for satellite and digital data transmission average about 1 bit per billion bits of data transmitted ($1:10^9$ bits), and it is reasonable to forecast that the electronic error propagated by a 3-foot length of transmission cable, which would be typical of an apparatus of this invention, would be substantially lower. A complete eight-day peptide synthesis run like the one described below in the Example would require the transmission of 153,000 bits of data; at the generally recognized error rate of $1:10^9$ bits, more than 6,500 replications of that eight-day synthesis could be made with the erroneous transmission of only one data bit. This error rate is obviously negligible in a statistical sense, but in a qualitative sense it is negligible also, in that the error is unlikely to distort epitope mapping by eliminating a possible mimotope.

To achieve the objectives, an apparatus for use with computer software and hardware, such as IBM PC/XT/AT compatible for IBM PS-2 series computers, has been developed. The indexer comprises a plurality of plates, each with a multiplicity of separate wells. A light source such as a light emitting diode (LED) is mounted in each well, thus allowing each well to be illuminated individually when the light source is so instructed by a computer. The configuration of the amino acid indexer and its interaction with machine driven sequencing programs will now be described in further detail with reference to the figures accompanying this disclosure.

Figure 2:
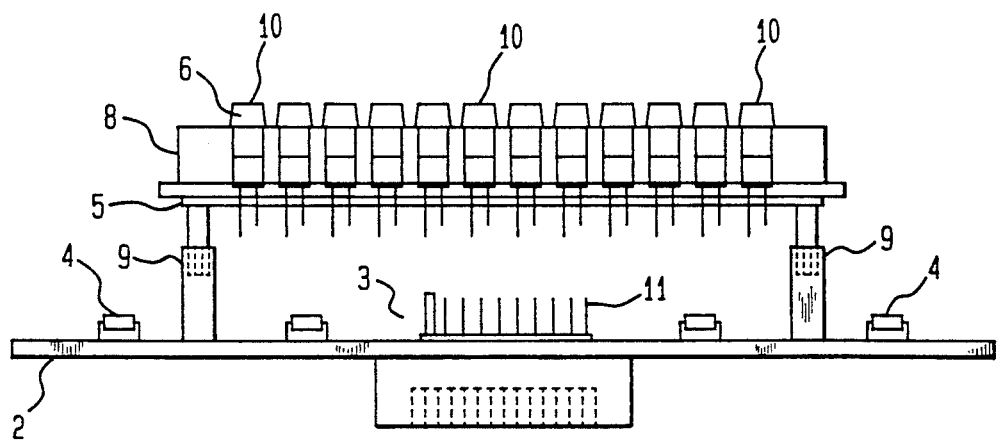
FIG. 2 is a side elevation of the combination of the invention depicted in top view in FIG. 1.

FIGS. 1 and 2 show, respectively, top and side views of light source arrays for microtiter plate well arrays (not shown) and related components of this invention. A sample plate with microtiter wells arrayed in this instance in a 8×12 well matrix is situated immediately atop an LED board 5 with an LED element 10 corresponding to each plate well in the array of the sample plate. The LED board 5 has a support structure 8 and the LED elements may optionally have collars 6 to collimate light beams under the microtiter plate wells. Pin connectors 9 connect the LED board 5 to a latch circuit board 2. The general configuration of chips 4 is shown on the latch circuit board 2 in both figures. The plate arrays are composed of these main elements: a sample plate, an LED board 5 (which includes an LED element 10 for each well in the array) and a latch circuit board 2 to drive the LEDs. Preferably, these elements are stationarily situated upon a base structure. Where multiple arrays are used, as is desired, the respective latch boards are connected to each other and to the main control board (not shown in FIGS. 1 and 2) with bus cables (also not shown).

Figure 3:
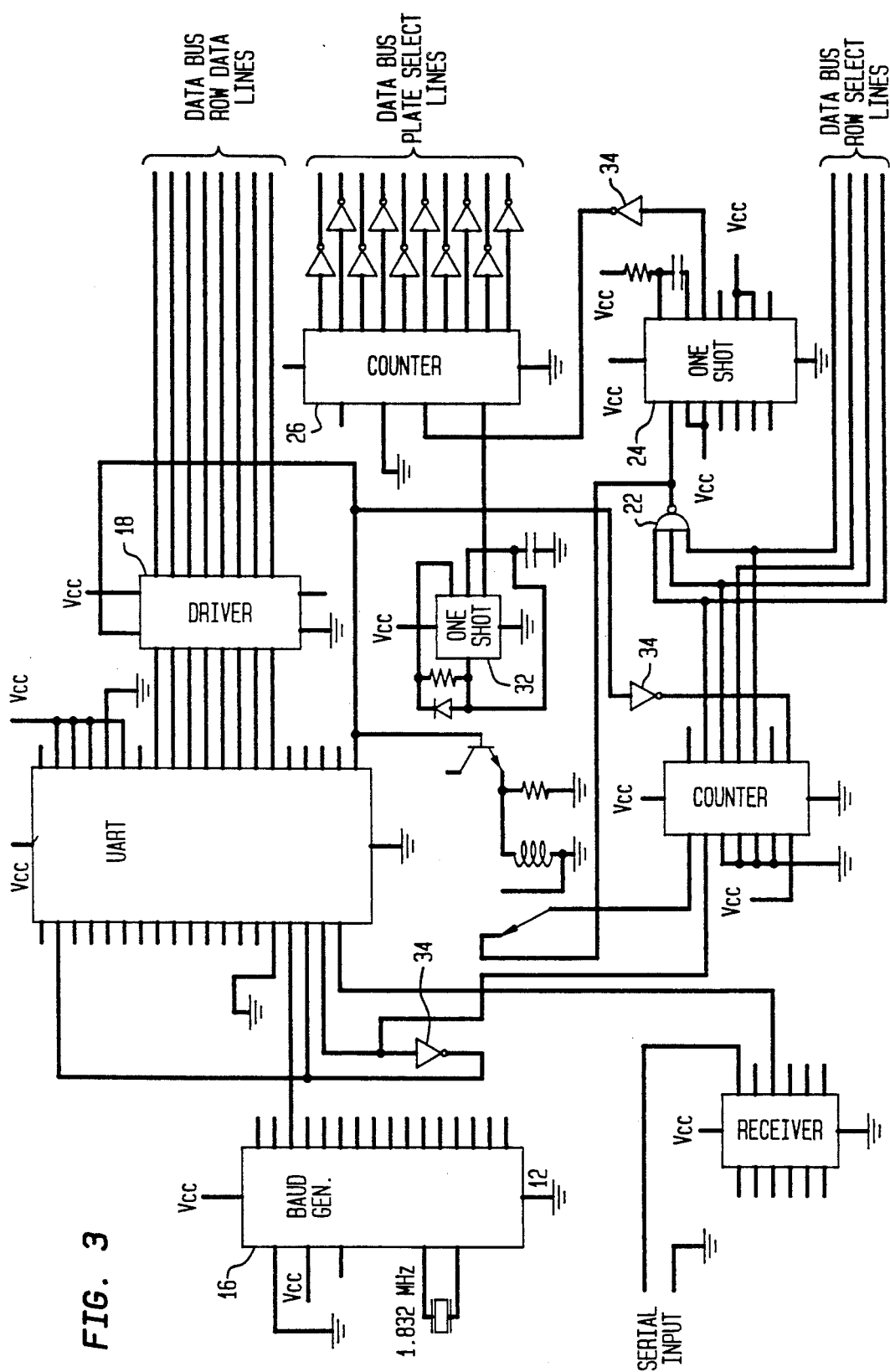
FIG. 3 is a schematic diagram of the main control circuit board of the invention.
Figure 4B:
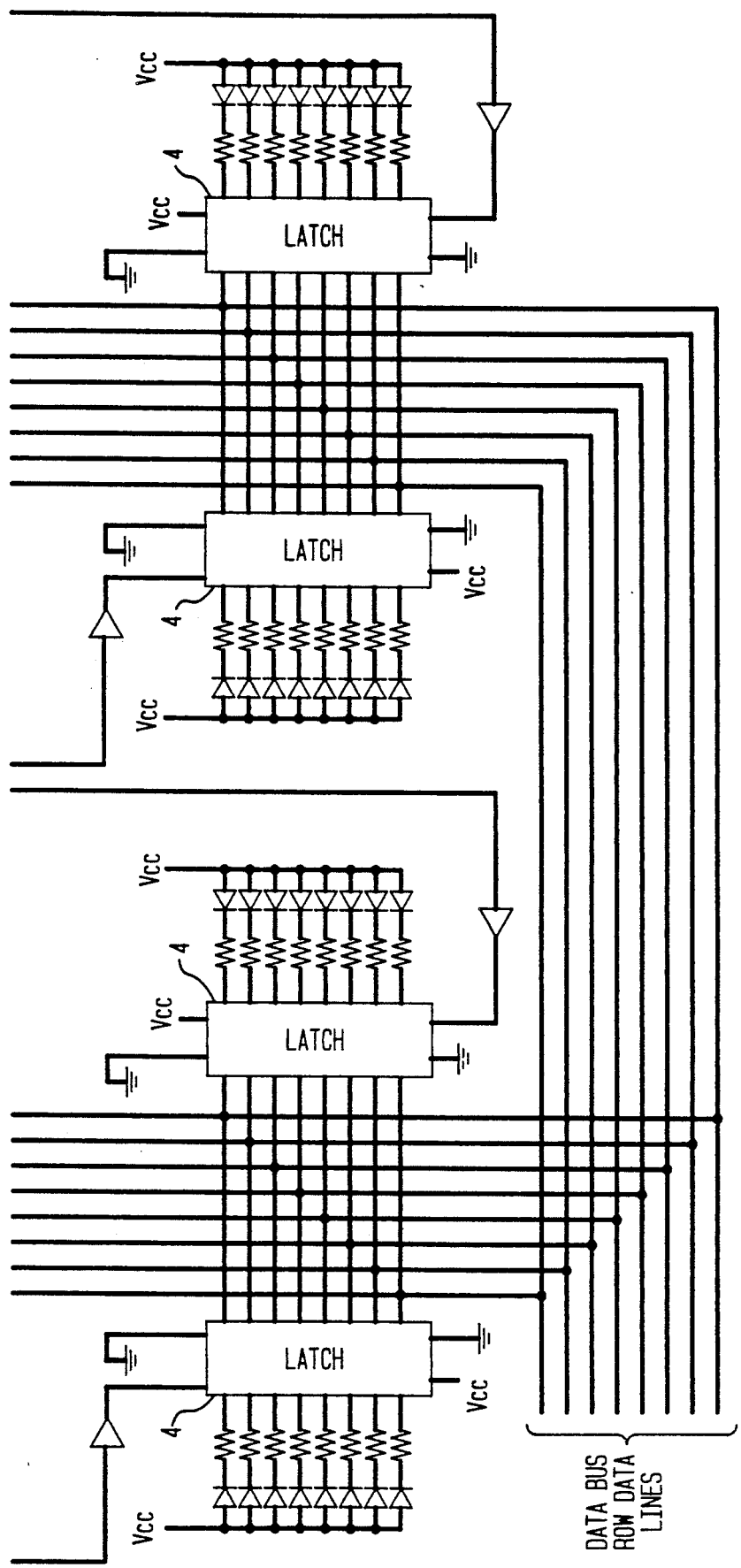
FIG. 4, comprised of FIG. 4A and 4B collectively, is a schematic diagram of a latch circuit board of the invention.

Circuit boards are shown in schematic diagrams in FIGS. 3 and 4. The main control board of the invention is shown in FIG. 3. The control board comprises several chips which are identified here with reference numerals corresponding to those in the figure. Data is received by a receiver chip 12 which converts the voltages to transistor-transistor logic (TTL) levels (for example, +5 vdc and 0 vdc). The signal is fed to a universal asynchronous receiver/transmitter (UART) chip 14. A baud rate generator chip 16 provides the correct clock frequency to the UART chip 14 to synchronize the rate of transmission of data bits from the UART with that being received from the computer. The UART output goes to an octal driver chip 18 which drives the data through a bus cable (not shown) to each latch board 2. A row counter chip 20 is incremented every time the UART chip 14 receives a character. Row count information is expressed in four data lines that are bussed to each of the latch boards 2. A 3-input AND gate 22 is used to reset the row counter chip 20 to zero. A one-shot chip 24 is pulsed when the counter chip 20 is reset, incrementing a one-of-ten counter chip 26. This chip is used to track which microtiter well plate is currently active. The ten data lines from the one-of-ten counter chip 26 pass through inverters 28 and 30 and are bussed to each latch board. The latch boards, depicted in FIG. 4, comprise a 4 to 16 line data distributor 3, twelve octal latches 4 and inverters 7. A one-shot chip 32 initializes all counters to zero when the apparatus is first turned on, and inverters 34 provide the correct polarity to chips 14, 20, and 26.

The latch boards 2 are chained together and connected to the main control board by a bus cable. The computer sends data via signals to the main control board using RS-232 asynchronous communication protocol. Where a 8×12 matrix is used, such as the sample plate matrix described above, a standard 8 bit American Standard Code for Information Interchange (ASCII) code may be used. In this code, a single 8-bit character represents the light pattern of each row of each 8×12 LED matrix (each bit corresponds to a single well). If a bit has a high TTL level (+5 vdc, for example), the corresponding LED will be off; if a bit has a low TTL level (0 vdc, ground, for example), the corresponding LED will be illuminated. If, as described here, ten plates each having an 8×12 matrix are used, then the main control board transmits to the indexer 130 ASCII characters for each amino acid, or one character for each of twelve rows for each of the ten plates, plus one null character per plate to reset the counter.

Figure 5:
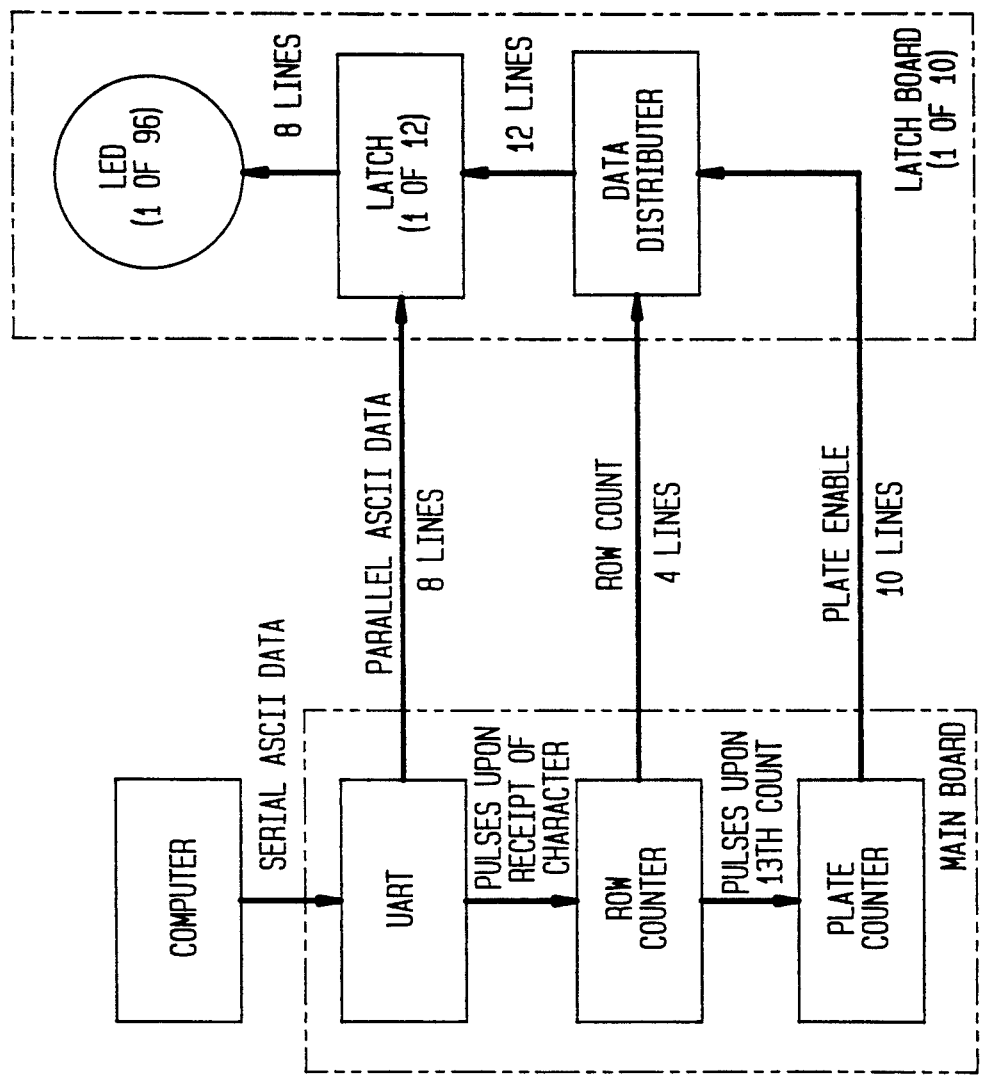
FIG. 5 is a flow diagram depicting the logic sequence of the electronic elements of the invention.

The bus cable is comprised of twenty-six conductors. Eight lines carry the character data which actually illuminates the LEDs in the proper sequence in accordance with the amino acid profile in the computer. Ten lines carry the active plate information (where ten different plates are employed) while four lines carry the plate row data and 4 lines are used to provide the high voltage and ground signals. Each latch board has access to all the bus information simultaneously. The individual latch boards 2 are addressed (from 1 to 10 where a ten board apparatus is in use) by a shorting block 11. The addresses correspond to the ten active plate lines from the main control board. When the active plate line corresponding to a latch board address is high (+5 vdc), the 4 to 16 line data distributor 3 on the latch board is activated. The data distributor 3 decodes the four plate row data lines and after being inverted (inverters 7) activate the corresponding octal latch which latches the character data from the bus and illuminates the appropriate LEDs. As each character is passed down the data bus, it is passed onto one of the twelve octal latches 4 on one of the latch boards 2. The interrelationships of the programmed computer, the main control circuit board, and the latch circuit boards of the invention are depicted in the flow chart set forth in FIG. 5.

Apparatuses for peptide synthesis comprising a computer, plate well arrays, and illumination means for wells may be used in conjunction with a variety of main circuit board control means and electronic latching means differing from the circuits depicted in FIGS. 3 and 4 and described herein. In a preferred embodiment, the main circuit control board comprises a TTL receiver chip for receiving amino acid sequencing and selection data impulse signals from a computer, a universal asynchronous receiver/transmitter chip, a baud rate generator chip, an octal driver chip, a row counter chip, a 3-input AND gate, a one-shot chip, a one-of-ten counter chip, and ten inverters. The latch boards of the preferred embodiment comprise a 4 to 16 line data distributor chip, twelve octal latches, and two inverters. The latch boards are connected to each other and to the main control board in the preferred embodiment by a bus cable comprised of conductors for each of the plates to carry plate activity data, for each row of the standard matrix to carry LED illumination data, for plate row selection and for high or ground voltage data. Where ten plates, each comprising an 8×12 plate well matrix, are employed, the bus cable would have twenty-six conductors: ten for plate activity, eight high/low voltage data for LED illumination, four for plate row selection, two for power and two for ground. In the preferred embodiment, each LED board and its respective latch control board are connected by two 50-pin connectors 9. Ten plates, each having an 8×12 plate well matrix, capable of carrying the synthesis of 960 different peptide chains, are employed in this apparatus.

A particular application of the apparatus and method of this invention in synthesizing peptides according to the 8-catamer system introduced by H. M. Geysen, cited above, is presented in the following Example.

EXAMPLE

Software was designed specifically for synthesizing peptides according to the Geysen system using an apparatus of the invention and following the method of the invention. The software program reads a protein sequence, in this case the protein sequence shown in FIG.

Figure 7:
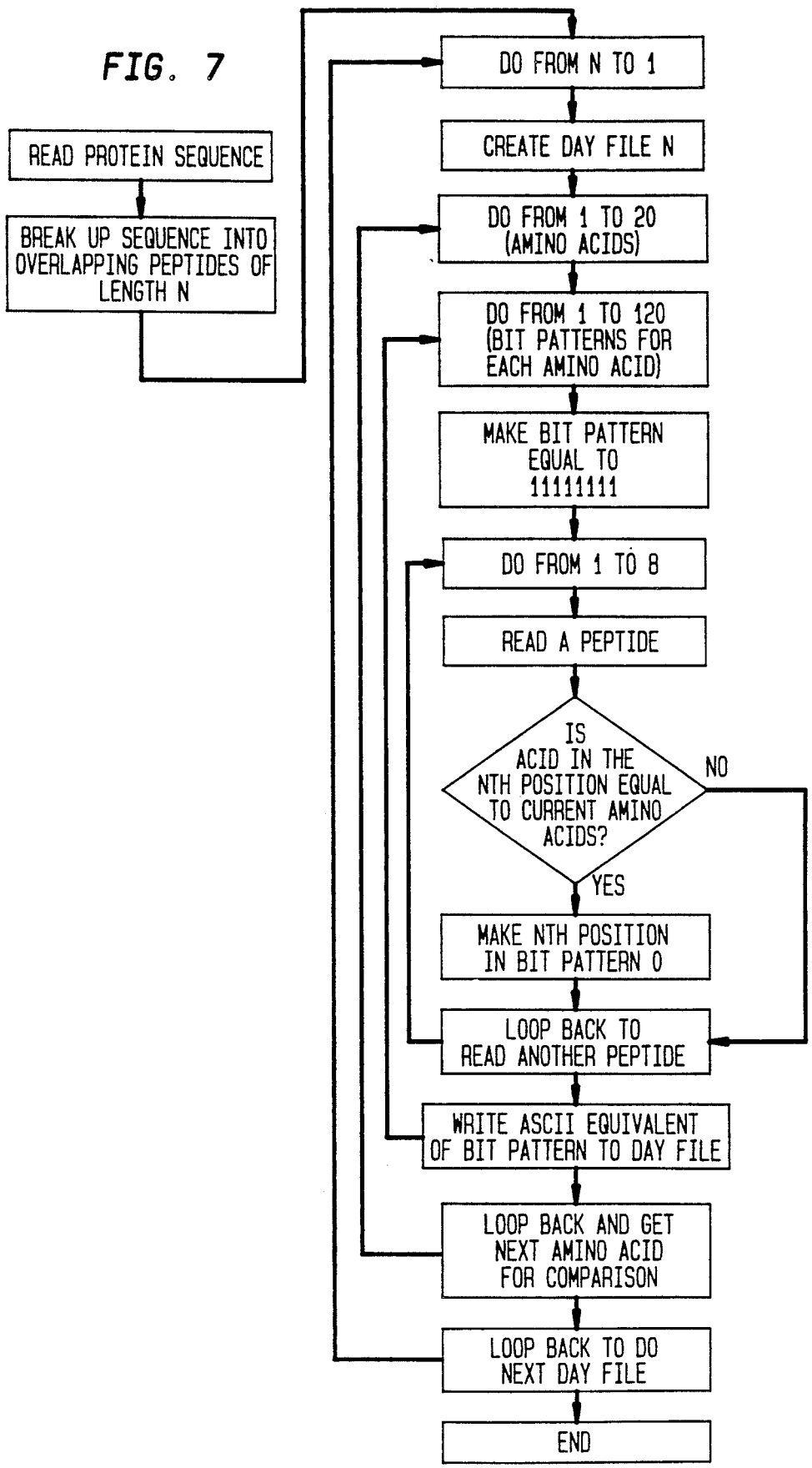
FIG. 7 is a bit pattern file software flow chart showing the logic of the amino indexing and selection software used in the peptide syntheses described in the Example.

6, and creates separate pattern files. Since peptides containing eight residues each were being prepared in this Example, eight separate pattern files were created (one day was devoted to placing an amino acid residue in each well according to the sequence instructed by the computer, so eight days in all were required for the syntheses of this Example). Pattern files contain information to instruct the indexer apparatus as to which amino acid should be placed in which plate well on each of eight succeeding days of the synthesis exercise. The logic of the software designed for mimotope peptide synthesis as performed in this Example is depicted in the flow chart set forth in FIG. 7. The amino acid index apparatus used in this example employed ten solvent-resistant microtiter plates, each comprising an 8×12 matrix of wells. Solvent-resistant empty plates were laid atop LED indicator plates, each having a 8×12 matrix of LEDs to correspond to the well matrix arrangement, allowing LEDs to illuminate their corresponding wells individually.

The software designed for this exercise provided five main menu choices of function: (1) Create Peptide Sequence; (2) Implement Sequence; (3) Print Report; (4) Test Hardware; and (5) ELISA Analysis. The apparatus was assembled as described, viz., with 8×12 solvent-resistant plate arrays placed atop 8×12 LED arrays, connected to an LED latch control board. Ten plate arrays containing 96 wells each were set up. The plates were connected to the main control circuit with a twenty-six conductor bus cable. An IBM PC AT was used. Solutions containing each of the twenty amino acids were prepared.

The synthesis sequence was begun by selecting menu choice (1), Create Peptide Sequence. Once the peptide sequence was created, the program created a comprehensive report detailing each peptide string that was to be synthesized, sized, the amounts of the respective amino acids that were to be used each day to complete the syntheses, and the eight pattern files that would be used to light the LEDs on the amino acid indexer in the patterns required for synthesis of 960 unique peptide strings. The report may be printed at the option of the researcher (menu choice (3)).

Synthesis of peptide strings was begun with the selection of menu choice (2), Implement Sequence. The program prompted the researcher to the correct pattern file for the appropriate day of the synthesis exercise. When the pattern file for the appropriate day was selected, a list of the twenty amino acids was displayed to the screen. The researcher can select amino acids in any order for placement in the solvent-resistant microtiter plate wells. When the Insert key was depressed, the software sent appropriate signals to the amino acid indexer to illuminate the wells into which reagent containing the amino acid selected was to be deposited. When the researcher had dispensed reagent containing the acid into each illuminated well, the Insert key was again depressed and another illumination pattern corresponding to a different amino acid was displayed. Reagent containing this acid was dispensed into each illuminated well. This procedure was repeated for each of the twenty amino acids until all 960 wells had been filled with its one amino acid. To effect peptide chain growth on the solid phase support, a solvent-resistant support suitable for ELISA analysis, such as a polystyrene bead or a polyethylene pin, was placed in each well after the researcher had dispensed therein the first amino acid residue. The Sequence Implementation procedure was repeated each day for eight days to complete the peptide syntheses. The finished peptide remains covalently bound to the support. It may then be analyzed on the solid phase or chemically cleaved and tested in solution.

Referring now to FIG. 6, the sequencing worked in the following manner: Looking at the code symbols for the first twenty amino acids of the test protein we see the following sequence:

MKKIMLIASA MSALSLPFSA

For the first eight peptide strings containing eight amino acids each (discounting controls comprising smaller fragments that were used in the exercise), the software signalled the indexer to prepare peptide strings in the following sequences pursuant to the overlap pattern introduced by Geysen:

1. MKKIMLIA
2. KKIMLIAS
3. KIMLIASA
4. IMLIASAM
5. MLIASAMS
6. LIASAMSA
7. IASAMSAL
8. ASAMSALS

Since the peptides were synthesized in reverse order, amino acids A,S,A, M,S,A,L,S were delivered to wells 1 through 8, respectively, of the first plate on the first day of synthesis. This is confirmed by reading the one letter code for the last amino acid of each peptide fragment vertically down the list of eight given above, from top to bottom. During the first day's synthesis, when the researcher requested the LED pattern for Alanine (A) to be displayed, the bit pattern 01011011 was sent to the first row and LEDs in positions 1,3, and 6 were lit, indicating that a solution containing Alanine was to be placed in wells 1,3 and 6 of the first plate (a 0 in the bit pattern indicates a lit LED). Continuing with this illustration, on the second day when the researcher requested the LED pattern for Arginine (R), the bit pattern 11111111 was sent to the first row; when the LED pattern for Alanine (A) was requested, the bit pattern 10101101 was sent to row 1 of plate 1, indicating that a solution containing the amino acid Alanine was to be placed in wells 2,4 and 7. It is important to note that this brief illustration covers the first eight peptides while the indexer is designed always to receive (in a 960 fragment synthesis using ten 8×12 well arrays) 120 8-bit patterns for each amino acid (8 rows×12 columns×10 plates). To complete the illustration, 119 appropriate bit patterns would have been sent to the indexer for each acid after the first row bit patterns were sent, as described above. The software used in the syntheses of this Example created the appropriate number of day files (8 in this instance), each consisting of 2400 bit patterns (120 patterns×20 amino acids). To simplify the process, each 8-bit pattern was represented by its ASCII character equivalent, thus allowing the use of existing DOS operating system software to send the pattern files to the indexer.

The overlapping pattern continued in the manner following this pattern through the synthesis of 960 peptide strings beginning with the first eight amino acids of the protein sequence of FIG. 6. The syntheses were completed in one-sixth the time that purely manual syntheses of the same number of peptide strings would have taken, at a negligible error rate.

Having been given the teachings of this invention, variations and ramifications will occur to those skilled in this art. Thus, even though highly specific circuit configurations for the main control board and the latch boards have been described in a preferred embodiment, other arrangements are obviously feasible. Further, whereas an apparatus with ten plates, each having 96 wells arranged in 8×12 matrices, has been illustrated, other matrices and differing numbers of plates may be employed. Additionally, although syntheses of 8-residue peptides following Geysen were illustrated, the apparatus and method can be used in other biochemical techniques, including syntheses of peptide strings having more or less then eight residues each. Different kinds of software can be custom designed to meet the particular needs of specific applications of the apparatus and method of this invention. These and other modifications occurring to those skilled in the art are deemed to be within the scope of this invention.

What is claimed is:

1. An apparatus for indexing of amino acids and incremental synthesis of peptides comprising:
   (a) input means for receiving amino acid selection and sequencing instructions and amino acid indexing signals for peptide synthesis;
   (b) control means connected to said input means for receiving said indexing signals and translating said indexing signals to produce control signals;
   (c) a base structure;
   (d) lighting means connected to said control means by electrical conduction means, said lighting means having longitudinal and lateral dimensions and a plurality of light emitting members in an array, and each light emitting member being selectively activated in accordance with one of the control signals from said control means corresponding to an indexing signal; and
   (e) sample plate means disposed upon said base and aligned with the lighting means and having longitudinal and lateral dimensions corresponding to the lighting means, the sample plate means further having means for receiving sample plates having a plurality of wells for receiving amino acid solutions according to activated ones of the light emitting means and for receiving a solvent resistant support for peptide chain synthesis.

2. The apparatus of claim 1 further comprising: latch circuit board control means connected to the control means to power and illuminate the lighting means in accordance with control signals received from said control means.

3. The apparatus of claim 2 wherein the sample plates comprises ten discrete sample plates, wherein each sample plate comprises 96 wells arrayed in an 8×12 matrix and the lighting means comprises 96 individual light emitting diode elements arrayed in an 8×12 matrix wherein each light emitting diode element corresponds uniquely to one well of the sample plate.

4. The apparatus of claim 3 in which the control means comprises:
   (a) a TTL logic chip for receiving signals from said input means and converting the signals to TTL logic levels;
   (b) a UART chip for converting signal characters received from the TTL chip from serial to parallel bit transmission modes and transmitting the converted signals to an octal driver chip;
   (c) a baud rate generator chip for providing clock frequency to the UART chip to synchronize operation with the input means;
   (d) an octal driver chip to drive the UART signals at appropriate clock frequency received from the UART chip;
   (e) a row counter chip connected to the UART chip, for expressing row count information to each latch board control means;
   (f) a 3-input AND gate for resetting the row counter chip to zero;
   (g) a first one-shot chip which is pulsed when the row counter chip is reset, thus incrementing a one-of-ten counter chip;
   (h) a one-of-ten counter chip for maintaining a count value indicative of the sample plate;
   (i) ten inverters through which ten plate select lines are bussed;
   (j) a second one-shot chip to reset all counters at zero when power is first supplied to the apparatus; and
   (k) three inverters to provide correct TTL signal polarity respectively to the UART chip, the row counter chip, and the plate counter chip.

5. The apparatus of claim 3 in which the latch circuit board control means comprise:
   (a) a shorting block for receiving plate address signals from the control means;
   (b) a 4-16 line data distributor for decoding plate row data line input signals to activate a corresponding octal latch;
   (c) twelve octal latches to control illumination of the individual light emitting diode elements; and
   (d) inverters to control the polarity of signals transmitted to each octal latch.

6. The apparatus of claim 3 in which:
   A. the control means comprise:
      (a) a TTL logic chip for receiving signals from said input means and converting the signals to TTL logic levels;
      (b) a UART chip for converting signal characters received from the TTL chip from serial to parallel bit transmission modes and transmitting the converted signals to an octal driver chip;
      (c) a baud rate generator chip for providing clock frequency to the UART chip to synchronize pulses with the input means;
      (d) an octal driver chip to drive the UART signals at appropriate clock frequency received from the UART chip;
      (e) a row counter chip for expressing row count information to each latch board control means;
      (f) a 3-input AND gate for resetting the row counter chip to zero;
      (g) a first one-shot chip which is pulsed when the row counter chip is reset, thus incrementing a one-of-ten counter chip;
      (h) a one-of-ten counter chip for maintaining a count value indicative of each sample plate;
      (i) ten inverters through which ten plate select lines are bussed;
      (j) a second one-shot chip to reset all counters at zero when power is first supplied to the apparatus; and
      (k) three inverters to provide correct TTL signal polarity respectively to the UART chip, the row counter chip, and the plate counter chip, and
   B. the latch circuit board control means comprise:
      (a) a shorting block for receiving plate address signals from the control means;

(b) a 4–16 line data distributor for decoding plate row data line input signals to activate a corresponding octal latch;

(c) twelve octal latches to control illumination of the individual light emitting diode elements; and (d) inverters to control the polarity of signals transmitted to each octal latch.

7. An automated method for sequential peptide synthesis comprising the steps of:

(a) providing instructions indicative of selection and sequencing of amino acids to an apparatus for peptide synthesis;

(b) generating signals to control illuminated patterns of light emitting diodes corresponding to wells in sample plates;

(c) depositing within illuminated sample plate wells a particular amino acid in accordance with the signals;

(d) repeating said steps until each well in each sample plate has received an amino acid;

(e) depositing within sample plate wells a solvent-resistant support means for peptide synthesis; and (f) repeating all of the foregoing steps until amino acids have been deposited into each well of each sample plate to form peptides of selected amino acids and sequence.

* * * * *